United States Patent [19]

Ferguson et al.

[11] 4,384,034
[45] May 17, 1983

[54] THIOPYRYLIUM DYE SENSITIZED PHOTOCONDUCTIVE MATERIALS

[75] Inventors: Alan N. Ferguson, White Bear Lake, Minn.; Kenneth Reynolds, Harlow, England

[73] Assignee: Minnesota Mining and Manufacturing Company, St. Paul, Minn.

[21] Appl. No.: 239,013

[22] Filed: Feb. 27, 1981

[51] Int. Cl.³ .............................................. G03G 5/09
[52] U.S. Cl. ...................................... 430/83; 430/82; 430/91; 430/95; 430/900
[58] Field of Search ...................... 430/82, 83, 91, 95, 430/900

[56] References Cited

U.S. PATENT DOCUMENTS

| | | | |
|---|---|---|---|
| 3,250,615 | 5/1966 | Van Allan et al. | 430/95 X |
| 3,557,088 | 1/1971 | Klingsberg | 260/239 |
| 3,577,235 | 5/1971 | Coltois | 430/83 X |
| 3,615,414 | 10/1971 | Light | 96/1.6 |
| 3,909,260 | 9/1975 | Seoka et al. | 430/82 X |
| 4,167,412 | 9/1979 | Regan et al. | 430/83 |

Primary Examiner—Roland E. Martin, Jr.
Attorney, Agent, or Firm—Cruzan Alexander; Donald M. Sell; Mark A. Litman

[57] ABSTRACT

A photoconductive layer sensitized by a compound of the general formula:

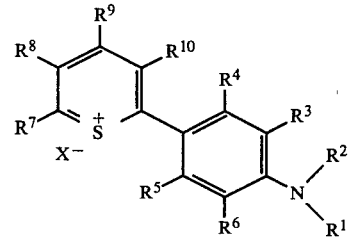

in which:

$R^1$ and $R^2$ independently represent a hydrogen atom, an alkyl or substituted alkyl group, an aryl or substituted aryl group, an aralkyl or substituted aralkyl group, a cycloaliphatic or substituted cycloaliphatic group or a heterocyclic or substituted heterocyclic group providing $R^1$ and $R^2$ do not both represent cyclic groups of aromatic nature, or $R^1$ and $R^2$ together may represent the necessary atoms to complete a non-aromatic heterocyclic ring, $R^3$, $R^4$, $R^5$ and $R^6$ independently represent a hydrogen atom or any substituent providing the sum of their $\sigma_p$ constants has a value of less than +0.5, or $R^3$ and $R^4$ and/or $R^5$ and $R^6$ may represent the necessary atoms to complete an alicyclic or aromatic ring, $R^3$ and $R^2$ and/or $R^1$ and $R^6$ may represent the necessary atoms to complete a non-aromatic heterocyclic ring, $R^7$ and $R^9$ independently represent a hydrogen atom or any carbon linked substituent containing up to 16 carbon atoms, $R^8$ and $R^{10}$ independently represent a hydrogen atom, an alkyl group having 1 to 4 carbon atoms or any two adjacent substituents $R^7$, $R^8$, $R^9$ and $R^{10}$ together may complete an alicyclic or aromatic ring, and $X^-$ represents an anion.

8 Claims, No Drawings

THIOPYRYLIUM DYE SENSITIZED PHOTOCONDUCTIVE MATERIALS

FIELD OF THE INVENTION

This invention relates to thiopyrylium compounds, to their preparation and to their use as photoconductors or sensitizers in photosensitive elements for image recording. In particular the invention relates to 2-(4-aminophenyl)thiopyrylium compounds.

BACKGROUND OF THE INVENTION

Photoconductive elements have achieved a broadly based acceptance in commercial technology. Almost all of these systems utilize the phenomenon exhibited by certain materials to change their conductivity when struck by radiation to which they are sensitive and thus are able to selectively discharge accumulated electrical charges. One important area of research in this technical area has been an effort to sensitize these photoconductive materials to different and more useful portions of the electromagnetic spectrum and to increase the efficiency of the photoconductive effect.

Electrophotographic imaging systems are well known in the art, as shown, for example, in U.S. Pat. Nos. 2,221,776; 2,277,013; 2,825,814; 3,220,831; 3,615,414, and others.

One generally accepted type of unitary photoconductive construction comprises a substrate having a conductive layer on at least one surface and a photoconductive composition over said conductive layer. The inclusion of photosensitizing materials or adjuvants to the photoconductive material is conveniently used to change the sensitivity and/or speed of the construction, as shown in U.S. Pat. Nos. 2,987,395 and 3,250,615.

U.S. Pat. No. 3,615,414 discloses the use of particulate discontinuous phases of pyrylium dyes in electrically insulating polymeric materials containing photoconductors to sensitize the photoconductive layer. Difficult and complex processing to effect the dispersion and agglomeration of the particle phases are disclosed therein to achieve some expansion of the range of spectral response for the photoconductors.

SUMMARY OF THE INVENTION

According to the present invention there is provided a method of preparing a compound of the general formula:

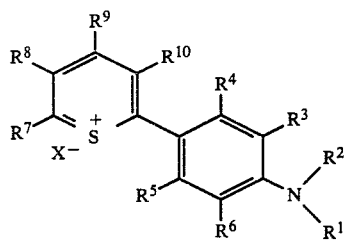

in which:

$R^1$ and $R^2$ independently represent a hydrogen atom, an alkyl or substituted alkyl group (preferably of up to 20 carbon atoms, more preferably of 1 to 8 carbon atoms), an aryl or substituted aryl group (preferably of up to 20 carbon atoms, more preferably phenyl), an aralkyl or substituted aralkyl group (preferably of up to 20 carbon atoms, preferably up to 10 carbon atoms), a cycloaliphatic or substituted cycloaliphatic group (preferably of 3 to 6 ring atoms) or a heterocyclic or substituted heterocyclic group (preferably of C, S, N and O atoms in 5, 6 or 7 membered rings) providing $R^1$ and $R^2$ do not both represent cyclic groups of aromatic nature, or $R^1$ and $R^2$ together may represent the necessary atoms to complete a non-aromatic heterocyclic ring comprised of C, S, N and O ring atoms, preferably of 5, 6 or 7 ring atoms, e.g. morpholine ring, $R^3$, $R^4$, $R^5$ and $R^6$ independently represent a hydrogen atom or any substituent providing the sum of their $\sigma_p$ constants (Hammet sigma, para) has a value of less than +0.5, preferably +0.4, or $R^3$ and $R^4$ and/or $R^5$ and $R^6$ may represent the necessary atoms to complete an alicyclic or aromatic ring (preferably of 5, 6 or 7 ring atoms, preferably selected from C, S, N and O, preferably of up to 20 carbon atoms on the group), $R^3$ and $R^2$ and/or $R^1$ and $R^6$ may represent the necessary atoms to complete a non-aromatic heterocyclic ring (preferably comprised of C, S, N and O ring atoms, preferably with 5, 6 or 7 ring atoms, preferably with up to 20 carbon atoms in the group), $R^7$ and $R^9$ independently represent a hydrogen atom or any carbon linked substituent containing up to 16 carbon atoms, preferably hydrocarbons such as alkyl and phenyl groups (preferably up to 4 carbons in the former and up to 10 carbons in the latter), $R^8$ and $R^{10}$ independently represent a hydrogen atom, an alkyl group having 1 to 4 carbon atoms, a phenyl group, or any two adjacent substituents $R^7$, $R^8$, $R^9$ and $R^{10}$ together may complete an alicyclic or aromatic ring (preferably hydrocarbon aromatic rings, most preferably benzene groups, substituted or not), and $X^-$ represents an anion, comprising reacting an amine of the general formula:

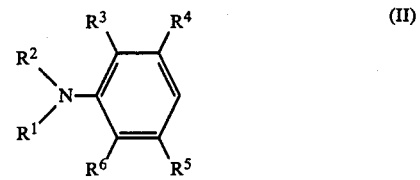

in which $R^1$ to $R^6$ are as defined above, with a thiopyrylium salt of the general formula:

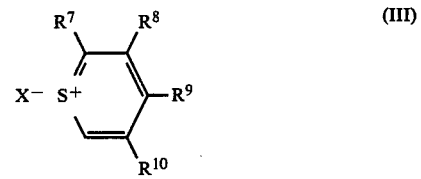

in which $X^-$ and $R^7$ to $R^{10}$ are as defined above, to yield the desired compound.

The invention also extends to the preparation of compounds of general formula (I) in their basic form by treatment of the salt with a base, e.g. sodium hydroxide.

Many of the compounds prepared by the method according to the invention are new and therefore the invention also provides compounds of general formula (I) disclosed above including those in their basic form in which $R^1$ to $R^{10}$ and $X^-$ are as defined above with the proviso that when $R^1=R^2=CH_3$ and $R^7=R^9=C_6H_5$ at least one of $R^3$ to $R^6$, $R^8$ and $R^{10}$ is other than a hydrogen atom. Many of these compounds have been found to autoassociate within photoconductive insulator layers and therefore not require the extraordinary processing requirements disclosed in U.S. Pat. No. 3,615,414.

The method of the invention may be conducted in a suitable solvent, e.g. alcohols such as ethanol, in many cases under gentle warming, or at reflux temperature. The products are generally slightly soluble in the cold reaction mixture.

The method of the invention is capable of preparing a wide range of compounds characterized by general formula (I). The amines of general formula (II) used as a starting material are readily available.

DETAILS OF THE PRESENT INVENTION

Many of the thiopyrylium salts of general formula (III) may be prepared according to the method disclosed by D. McKinnon in Canad. J. Chem. 48, 338 (1970) in which 2H-thipoyran-2-ones and 4H-thiopyran-4-ones are reduced with lithium aluminium hydride to give the corresponding thiopyranols and these pseudobases were converted to the thiopyrylium perchlorates using perchloric acid. Thus the hydride reduction of thiopyranones provides a convenient route to thiapyrylium salts via the thiopyranol pseudo-bases.

A number of other routes for the preparation of thiopyrylium salts within general formula (III) are disclosed in the literature which enable production of all of the compounds of the present invention. For example, polycyclic thiopyrylium salts may be prepared according to the methods disclosed by B. D. Tilak, R. B. Mitra and Z. Muljiani, *Tetrahedron* 25, 1939 (1969) and S. D. Tindal and B. D. Tilak, *Indian J. Chem.* 7, 637 (1969).

In general compounds of general formulae (II) and (III) may have a wide range of substituents providing that in compound (II) there is a sufficiently high electron density in the para-position to the nitrogen and in compound (III) there is a sufficiently low electron density in the 2-position for the reaction to proceed.

The compounds of the invention are particularly useful as sensitizers or photoconductors and may be used, for example, in systems such as those disclosed in U.S. Pat. Nos. 3,250,615 and 3,615,414. The photosensitive elements generally comprise a support having coated theren a layer of electrically insulating film-forming resin. The resin may be photoconductive or may act as a binder for a photoconductive compound. The support is usually conductive or has an integral conductive layer thereon. The compounds of the invention may be used as the photoconductor in such elements but preferably are used as a sensitizer to enhance the photoconduction of the layer.

Typical classes of photoconductive materials useful in electrophotography include (1) inorganic crystalline photoconductors such as cadmium, sulfide, cadmium sulfoselenide, cadmium selenide, zinc sulfide, zinc oxide, and mixtures thereof, (2) inorganic photoconductive glasses such as amorphous selenium, selenium alloys, and selenium-arsenic, and (3) organic photoconductors such as phthalocyanine pigments and polyvinyl carbazole, with or without binders and additives which extend their range of spectral sensitivity. These systems are well known in the art. For example, U.S. Pat. No. 3,877,935 discusses various problems associated with the crystalline and amorphous classes of photoconductors and shows the use of polynuclear quinone pigments in a binder as a photoconductive layer. U.S. Pat. No. 3,824,099 shows the use of squaric acid methine and triaryl pyrazoline compounds as an electrophotographic charge transport layer. Cadmium sulfoselenide plates are shown in U.S. Pat. No. 3,764,315, and one of the original disclosures of the use of poly-N-vinylcarbazole as a photoconductive insulating layer is provided in U.S. Pat. No. 3,037,861. A number of diverse organic photoconductors have been disclosed since the development of the carbazole class of photoconductors such as quinones and anthrones (e.g., Hayashi et al., *Bull. Chem. Soc. Japan,* vol. 39, (1966) pages 1670–1673), but the carbazoles have continued to attract the greatest attention.

The use of carbazole condensates with aldehydes as shown in U.S. Pat. No. 4,025,341 are another useful class of organic photoconductors. Triaryl methanes including a carbazole moiety (as shown in Xerox Disclosure Journal, Vol. 3, No. 1, January/February 1978, page 7) are also useful photoconductive insulators as are the materials of Japanese Patent Publication No. 52-34735.

Various binder materials known in the art are useful with electronically active donor compounds useful in the present invention. It is of course preferred that the binder be essentially optically transparent or at least electronically active transparent to the wavelengths of radiation to which the compounds (sensitized or not) are sensitive. Amongst the useful binders are poly(vinyl chloride), poly(siloxanes), poly(vinyl butyral), poly(vinyl acetate), styrene/acrylonitrile copolymers, polyacrylates, polymethacrylates, polycarbonates, polyepoxides, polyurethanes, polyamides, polyethers, polyesters, polyolefins as well as block, graft, random, and alternating polymers, copolymers, terpolymers and mixtures thereof and the like. The binders are preferably electrically inactive themselves. The preferred polymeric binders are polycarbonates, polyacrylates, polyesters, and styrene/acrylonitrile copolymers. Coating aids, lubricants, surface active agents, other sensitizing dyes, and other adjuvants may be added to the composition.

For use of the materials of the present invention in electrophotographic layers, organic electron donor compounds should be present as at least 15 or 20 percent by weight of the composition. Preferably the donor compound should be present as at least 25 or 35 percent by weight of the layer, and may comprise up to 100% by weight of the layer, excluding, of course, the sensitizer dye. The sensitizing dyes should be used in amounts which will increase the sensitivity of the composition. This is defined as an effective sensitizing amount of dye. Ordinarily amounts of from 0.01 percent by weight up to 10% or 15% by weight dye may be used. Certain constructions can be envisaged with as much as 90% by weight of dye and 10% by weight of organic electron donor compounds. Amounts of dye as small as 0.005 percent by weight can increase the sensitivity of the electron donor compounds. More preferred concentration ranges are between 0.05 and 10 percent by weight.

The photosensitive materials of the present invention may also be useful as photoconductive toners, photovoltaic devices, organic semiconductors, and the like, and may use concentrations of organic electron donor compounds as low as 5 percent by weight.

The photosensitive elements are utilized by imposing a uniform electrostatic charge on the surface of the insulating layer, exposing the charged surface imagewise to light to dissipate the charge only in the light-struck areas thereby forming an electrostatic image on the surface and thereafter developing a visible image by means of the electrostatic image.

With regard to the compounds of general formulae (I) to (III) $R^1$ and $R^2$ may represent a wide variety of substituents as stated above providing $R^1$ and $R^2$ are not both cyclic groups of aromatic character. We have found that when $R^1$ and $R^2$ are both cyclic groups, e.g. phenyl, the para-position of the phenyl ring is deactivated and reaction with the thiopyrylium salt will not occur. Preferred substituents for $R^1$ and $R^2$ include H, $CH_3$, $C_2H_5$, cyclo-$C_6H_{11}$, $CH_2CH_2OH$, $C_6H_5$ and $C_6H_5CH_2$.

$R^1$ and $R^2$ together with the nitrogen atom to which they are attached may form a non-aromatic heterocyclic ring, e.g. a morpholine ring:

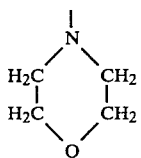

Also $R^1$ and $R^6$, and similarly $R^2$ and $R^3$, may represent the necessary atoms required to form a non-aromatic heterocyclic nucleus, for example:

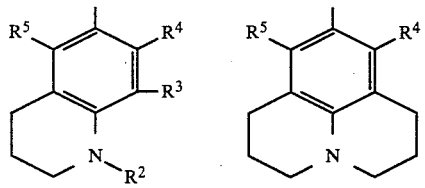

$R^3$ to $R^6$ may represent a hydrogen atom or any substituent provided that the sum of the $\sigma_p$ constants of $R^3$ to $R^6$ has a value less than +0.5. We have found that if the $\sigma_p$ exceeds +0.5 it is unlikely that the reaction will occur between the amine and thiopyrylium salt. Typical $\sigma_p$ values for substituents may be found in the literature, e.g. "A Critical Compilation of Substituent Constants", O. Exner, *Correllation Analysis in Chemistry*, Edit. Chapman and Shorter, Plenum Press 1968. Examples of $\sigma_p$ values are given in the following Table.

| | | | |
|---|---|---|---|
| Me | −0.14 | $NMe_2$ | −0.63 |
| Et | −0.13 | $NEt_2$ | −0.53 |
| $Pr^n$ | −0.15 | NHPh | −0.27 |
| $Pr^i$ | −0.13 | $NPh_2$ | −0.29 |
| $Bu^n$ | −0.19 | NHAc | −0.09 |
| cyclo.$C_6H_{11}$ | −0.13 | $NO_2$ | +0.81 |
| Ph | 0.05 | OH | −0.38 |
| $CH_2Ph$ | −0.06 | OMe | −0.28 |
| $CH_2OR$ | +0.02 | OEt | −0.14 |
| $CF_3$ | +0.53 | OPh | +0.14 |
| CHO | +0.47 | SMe | −0.07 |
| COMe | +0.47 | $SO_2Me$ | +0.73 |
| COOH | +0.44 | F | +0.15 |
| COOR | +0.44 | Cl | +0.24 |
| $NH_2$ | −0.30 | Br | +0.26 |
| NHMe | −0.46 | I | +0.21 |

$R^7$ and $R^9$ may represent a hydrogen atom or any carbon-linked substituent containing up to 16 carbon atoms. Preferably $R^7$ and $R^9$ are hydrogen, aryl or substituted aryl (preferably phenyl).

Any of the adjacent substituents $R^3$ to $R^{10}$ may represent the necessary atoms to form a fused-on carbocyclic or heterocyclic ring, preferably of 5, 6 or 7 ring atoms, with the heterocyclic rings preferably comprised of C, S, N and O atoms.

$X^-$ may be any anion, particularly acid anions, examples of which include $ClO_4^-$, $CF_3SO_3^-$, p-toluene sulfonate, and $BF_4^-$.

A number of characteristics of these compounds, particularly when used as sensitizers for photoconductors in both solvent and bulk (aggregated) systems, distinguish them from the materials of the prior art. In comparing compounds of the prior art, such as, for example, 4-(4-dimethylaminophenyl)-2,6-diphenylthiopyrylium perchlorate (compound 2 of U.S. Pat. No. 3,615,414) with their structurally closest counterparts of the present invention, such as 2-(4-dimethylaminophenyl)-4,6-diphenylthiopyrylium perchlorate, it has been noted that the compounds of the present invention tend to absorb radiation in longer wavelengths (e.g., greater than 700 nm and particularly greater than 750 nm) in the aggregate form and also absorb radiation in solution at longer wavelengths. This is an extremely important capability. It is also quite surprising that a modest structural shift of the position of substituents will cause this change. The dramatic nature of this change can be seen in assuming a relative speed of 100 for each aggregated dye at 700 nm. The prior art dye indicated above exhibits a relative speed of less than 10 in a given organic photoconductor at 750 nm while the dye of the present invention exhibits a relative speed of over 70 in the same photoconductor. Absolute speeds are also comparable at maximum absorbance, with less than 0.3 log units (usually less than 0.2 log units) variation between the dyes.

The invention will now be illustrated by the following Examples.

EXAMPLE 1

(a) Preparation of 4,6-diphenyl-α-dithiopyrone

Acetophenone (0.2 mole, 24 g) and pyrrolidine (0.24 mole, 77 g) were added to molecular sieves (Linde 5A) in anhydrous ether solution. The reaction mixture was shaken (100 hours) and then filtered. Molecular sieves were washed with ether (3×20 ml) and the combined filtrate was evaporated at 20 ml. 1-Pyrrolidinyl-1-phenylethylene was distilled (90° C., 0.25 mm) as an orange yellow oil (17.3 g 50%), and its boiling point was 74° to 76° C. 1-Pyrrolidinyl-1-phenylethylene (0.1 mole, 17.3 g) and carbon disulfide (40 ml) in anhydrous dioxane (40 ml) were heated (60° C., 3 hours). The excess of carbon disulfide was removed by distillation and a mixture of methanol (30 ml) and water (10 ml) was added. The product was extracted with chloroform and the solvent was evaporated. The residue on recrystallization from methanol-dioxane (1:1) gave 4,6-diphenyl-α-dithiopyrone, (16.8 g, 60%) as red needles. Its melting point was 114° to 115° C.

(b) Preparation of 2,4-diphenylthiopyrylium perchlorate

To the 4,6-diphenyl-α-dithiopyrene (16.8 g, 0.06 mole) suspended in acetic acid (680 ml) was added a 30% $H_2O_2$ aqueous solution (17 ml) and the mixture maintained at 30° C. The mixture became dark red in color then slowly lightened to yellow. After two hours, 70% perchloric acid (21 ml) was added to the solution.

Dilution with ether gave yellow needles of 2,4-diphenylthiopyrylium perchlorate which were recrystallized from acetic acid containing perchloric acid (13.2 g, 63.2%). Its melting point was 156° to 157° C. 2,4-diphenylthiopyrylium trifluoromethane sulfonate (51%, melting point 188° C.) and 2,4-diphenylthiopyrylium tetrafluoroborate (66%, melting point 165° C.) were prepared by a similar procedure but using trifluoromethanesulfonic acid or tetrafluoroboric acid to acidify the reaction mixture in place of perchloric acid.

(c) Preparation of 2-(4-aminophenyl)-4,6-diphenylthiopyrylium perchlorate 2,4-diphenylthiopyrylium perchlorate (1 g, 2.87 mmole) and aniline (0.54 g, 5.74 mmole) were heated in 10 ml of ethanol at 40° to 45° C. The reaction mixture was immediately colored deep blue. After stirring was continued for two hours, the reaction mixture was allowed to stand at room temperature to give blue needles of 2-(4-aminophenyl)-4,6-diphenylthiopyrylium perchlorate. This compound was recrystallized from a mixture of ethanol-chloroform.

Yield: 52%, 0.66 g, melting point 160° to 162° C.
Found: C, 62.25; H, 4.20; N, 2.74. $C_{23}H_{18}NSClO_4$
Calculated: C, 62.80; H, 4.10; N, 3.18.

$\lambda$ max. 584 (log $\epsilon$, 4.21), 367 (log $\epsilon$, 4.27); $\tau$ (DMSO-$d_6$) 1.42 (2H d thiopyrylium protons) 1.8–3.26 (16H, aromatic and $NH_2$ protons).

EXAMPLES 2 TO 29

The salts listed in the following Table 1 were prepared in a similar manner to that in Example 1 from 2,4-diphenylpyrylium salt and the appropriate amine.

Table 2 reports the analysis, $\lambda$ max and log $\epsilon$ max of each compound.

TABLE 1

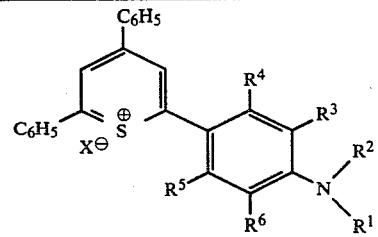

| Example No. | $R^1$ | $R^2$ | $R^3$ | $R^4$ | $R^5$ | $R^6$ | X | melting point °C. |
|---|---|---|---|---|---|---|---|---|
| 1 | H | H | H | H | H | H | $ClO_4$ | 160–162 |
| 2 | H | H | H | H | H | H | $CF_3SO_2$ | 207 |
| 3 | $CH_3$ | H | H | H | H | H | $ClO_4$ | 206–208 |
| 4 | $CH_3$ | H | H | H | H | H | $CF_3SO_3$ | 216 |
| 5 | $CH_3$ | $CH_3$ | H | H | H | H | $CF_3SO_3$ | 216 |
| 6 | $CH_3$ | $CH_3$ | H | H | H | H | $BF_4$ | 250 |
| 7 | $C_2H_5$ | $C_2H_5$ | H | H | H | H | $CF_3SO_3$ | 145 |
| 8 | $C_2H_5$ | $C_6H_5CH_2$ | H | H | H | H | $CF_3SO_3$ | 174 |
| 9 | $C_2H_5$ | $C_6H_5CH_2$ | H | H | H | H | $ClO_4$ | 175 |
| 10 | $C_2H_5$ | $C_6H_5CH_2$ | H | H | H | H | $BF_4$ | 204 |
| 11 | $C_6H_5CH_2$ | $C_6H_5CH_2$ | H | H | H | H | $CF_3SO_3$ | 231 |
| 12 | H | H | $CH_3$ | H | H | H | $CF_3SO_3$ | 202 |
| 13 | H | H | $CH_3$ | H | H | H | $ClO_4$ | 250 |
| 14 | H | H | H | $CH_3$ | H | H | $CF_3SO_3$ | 220 |
| 15 | H | H | H | $CH_3$ | H | H | $ClO_4$ | 165–168 |
| 16 | $CH_3$ | $CH_3$ | H | $CH_3$ | H | H | $CF_3SO_3$ | 105 |
| 17 | H | H | $CH_3$ | H | H | $CH_3$ | $CF_3SO_3$ | 245–250 |
| 18 | H | H | $C_2H_5$ | H | H | $C_2H_5$ | $CF_3SO_3$ | 187 |
| 19 | H | cyclo $C_6H_{11}$ | H | H | H | H | $CF_3SO_3$ | 133 |
| 20 | H | $C_6H_5$ | H | H | H | H | $CF_3SO_3$ | 193 |
| 21 | H | H | $OCH_3$ | H | H | H | $CF_3SO_3$ | 167 |
| 22 | H | H | $OCH_3$ | H | H | H | $ClO_4$ | 248 |
| 23 | H | H | H | $OCH_3$ | H | H | $CF_3SO_3$ | 235 |
| 24 | H | H | H | $OCH_3$ | H | H | $ClO_4$ | 165 |
| 25 | H | H | H | $OCH_3$ | H | $OCH_3$ | $CF_3SO_3$ | 131 |
| 26 | $CH_2CH_2OH$ | $CH_2CH_2OH$ | H | H | H | H | $ClO_4$ | 63 |
| 27 | H | H | H | Cl | H | H | $CF_3SO_3$ | 107–109 |
| 28 | H | H | H | Cl | H | H | $ClO_4$ | 170–172 |
| 29 | H | H | $NH_2$ | H | H | H | $CF_3SO_3$ | 250 |

TABLE 2

| Example No. | Calculated | | | | Found | | | | $\lambda$ max. (CHCl$_3$) | log $\epsilon$ max. |
|---|---|---|---|---|---|---|---|---|---|---|
| | C | H | N | S | C | H | N | S | | |
| 1 | 62.8 | 4.1 | 3.2 | — | 62.2 | 4.2 | 2.7 | — | 584 (EtOH) | 4.21 |
| 2 | 58.8 | 3.6 | 2.8 | 13.1 | 59.4 | 3.3 | 3.1 | 13.1 | 592 | 4.34 |
| 3 | 63.5 | 4.4 | 3.1 | — | 63.0 | 4.6 | 3.3 | — | 596 (EtOH) | 4.38 |
| 4 | 59.6 | 4.0 | 2.8 | 12.7 | 62.3 | 3.9 | 2.7 | 13.1 | 633 | 4.55 |
| 5 | 60.3 | 4.2 | 2.7 | 12.4 | 61.0 | 4.0 | 2.5 | 12.4 | 624 | 4.77 |
| 6 | 66.0 | 4.8 | 3.1 | 7.0 | 67.5 | 4.2 | 3.4 | 6.4 | 622 | 4.86 |
| 7 | 61.6 | 4.7 | 2.6 | 11.7 | 63.0 | 4.6 | 2.6 | 11.6 | 638 | 4.50 |
| 8 | 65.2 | 4.6 | 2.3 | 10.5 | 64.6 | 4.2 | 2.2 | 10.4 | 620 | 4.53 |
| 9 | 68.9 | 5.0 | 2.5 | 5.7 | 70.6 | 4.2 | 2.7 | 5.9 | 615 | 5.18 |
| 10 | 70.5 | 5.2 | 2.6 | 5.9 | 72.4 | 4.4 | 2.8 | 5.7 | 620 | 5.05 |
| 11 | 68.1 | 4.5 | 2.1 | 9.6 | 67.8 | 3.9 | 2.0 | 9.7 | 602 | 4.50 |
| 12 | 59.6 | 4.0 | 2.8 | — | 62.8 | 3.8 | 2.7 | — | 600 | 4.32 |
| 13 | 63.5 | 4.4 | 3.1 | — | 62.9 | 4.6 | 3.0 | — | 596 (EtOH) | 4.32 |
| 14 | 59.6 | 4.0 | 2.8 | 12.7 | 59.5 | 3.3 | 3.1 | 12.5 | 564 | 4.30 |

TABLE 2-continued

| Example No. | Calculated C | H | N | S | Found C | H | N | S | λ max. (CHCl₃) | log ε max. |
|---|---|---|---|---|---|---|---|---|---|---|
| 15 | 63.5 | 4.4 | 3.1 | — | 63.6 | 4.7 | 3.2 | — | 556 (EtOH) | 4.16 |
| 16 | 61.0 | 4.5 | 2.6 | 12.1 | 60.8 | 4.6 | 2.7 | 12.1 | 616 | 2.30 |
| 17 | 60.3 | 4.3 | 2.7 | 12.4 | 62.1 | 3.8 | 2.6 | 12.3 | 600 | 4.32 |
| 18 | 61.6 | 4.8 | 2.6 | 11.7 | 62.1 | 4.6 | 2.5 | 12.3 | 602 | 4.32 |
| 19 | 63.0 | 4.9 | 2.4 | 11.2 | 63.0 | 4.8 | 2.6 | 10.8 | 634 | 4.31 |
| 20 | 63.7 | 3.9 | 2.5 | 11.3 | 63.2 | 3.6 | 2.2 | 12.0 | 650 | 4.39 |
| 21 | 57.8 | 3.8 | 2.7 | 12.3 | 59.4 | 3.7 | 2.6 | 12.5 | 612 | 4.32 |
| 22 | 61.3 | 4.3 | 3.0 | — | 61.2 | 4.4 | 2.6 | — | 588 (EtOH) | 4.19 |
| 23 | — | — | 2.7 | 12.3 | — | — | 2.2 | 12.3 | 586 | 4.27 |
| 24 | 61.3 | 4.3 | 3.0 | — | 61.2 | 4.4 | 2.6 | — | 566 (EtOH) | 4.16 |
| 25 | 56.8 | 4.0 | 2.5 | 11.7 | 57.3 | 3.6 | 2.5 | 11.2 | 602 | 4.36 |
| 26 | 61.4 | 5.0 | 2.6 | 6.1 | 60.7 | 5.1 | 2.7 | 6.5 | 638 | 4.31 |
| 27 | 55.0 | 3.2 | 2.7 | 12.2 | 56.5 | 3.2 | 2.2 | 10.8 | 564 | 4.00 |
| 28 | — | — | — | — | — | — | — | — | 588 (EtOH) | 4.06 |
| 29 | 57.1 | 3.8 | 5.6 | 12.7 | 56.7 | 3.2 | 5.6 | 14.1 | 654 | — |

EXAMPLE 30

Preparation of 2,4-diphenyl-6(1,2,3,4-tetrahydroquinolin-6-yl) thiopyrylium trifluoromethane sulfonate 2,4-diphenylthiopyrylium trifluoromethane sulfonate (2.0 g) and 1,2,3,4-tetrahydroquinoline (1.4 g) in ethanol (20 ml) were heated at 90° for 30 minutes. After cooling the solution was poured into ether (50 ml) and the precipitated dye was filtered, washed with ether and recrystallized from ethanol as black needles having a melting point of 233° C., λ max (CHCl₃) 656 nm.

Found: C, 60.4; H 4.2; N, 2.6; S, 12,3. $C_{27}H_{22}F_3NSO_3$ Calculated: C, 61.2; H, 4.2; N, 2.6; S, 12.1.

EXAMPLE 31

Preparation of 2,4-diphenyl-6(julolidin-6-yl) thiopyrylium trifluoromethane sulfonate The same procedure as Example 30 was adopted using 2,4-diphenylthiopyrylium trifluoromethane sulphonate (2.0 g) and julolidine (1.7 g) in ethanol (20 ml). The dye was recovered in the form of black needles having a melting point of 211° C., λ max (CHCl₃) 675 nm.

Found: C, 62.5; H, 4.7; N, 2.5; S. 11.5. $C_{30}H_{26}F_3NSO_3$ Calculated: C, 63.3; H, 4.6; N, 2.5; S, 11.3.

EXAMPLES 32-35

Examples of Photoconduction Enhancement 5 g of a polycarbonate resin (Lexan ® 121, General Electric Corporation) were dissolved in 50 ml of 1,2-dichloro-ethane. To this solution were added 5 g of the photoconductor, 1,5-diphenyl-3-styryl-2-pyrazoline, and the mixture was stirred until the solution was complete. To 10 ml of this solution was added 0.01 g of a thiopyrylium dye from Table 1. When the dye had dissolved, the mixture was coated onto a thin aluminum sheet and dried, to give a film of 10 thickness. The film was then charged by a corona discharge to a surface potential, V, and then exposed to the light from a tungsten filament lamp in the instrument known as a Stati-Tester (manufactured by M/K Systems Inc.). The time required ($t_{\frac{1}{2}V}$) for the initial potential, V, of the film to drop to half its initial value is compared to that required for a coating containing photoconductor but no dye. The enhancement of photoconduction by the dyes of this invention is demonstrated in the following Table 3.

TABLE 3

| Dye, Table 1 | Initial Voltage (V) | $t_{\frac{1}{2}V}$ (sec.) |
|---|---|---|
| no dye | +615 | 43 |
| No. 2 | +610 | 0.8 |
| No. 4 | +555 | 0.9 |
| No. 15 | +625 | 1.0 |

EXAMPLES 36-49

5 grams of the polycarbonate resin of Examples 32-35 were dissolved in 50 ml of 1,2-dichloro-ethane. To this solution was added 5 grams of the photoconductor 1,5-diphenyl-3-styryl-2-pyrazoline and the mixture was stirred until dissolution was complete. To 10 ml portions of this solution were added 0.01 grams of the thiopyrilium dye indicated in the following table. When the dye had dissolved, the coating, drying and testing procedures of Examples 32-35 were repeated. The data are shown below.

| Example | Dye | Initial Voltage ($V_o$) (positive) | Time to Vo/2 (sec) |
|---|---|---|---|
| 36 | None | 615 | 43 |
| 37 | 2 | 610 | 0.8 |
| 38 | 4 | 555 | 0.9 |
| 39 | 5 | 700 | 0.7 |
| 40 | 7 | 540 | 1.6 |
| 41 | 11 | 210 | 1.1 |
| 42 | 12 | 365 | 1.0 |
| 43 | 14 | 525 | 0.9 |
| 44 | 15 | 625 | 1.0 |
| 45 | 16 | 600 | 1.0 |
| 46 | 17 | 345 | 1.0 |
| 47 | 18 | 350 | 0.3 |
| 48 | 27 | 780 | 5.4 |
| 49 | 29 | 585 | 11.2 |

EXAMPLES 50-60

The preparations and procedures of Examples 36-49 were repeated except that the photoconductor used was 5-(p-diethylaminophenyl)-3-(p-diethylaminostyryl)-1-phenyl-2-pyrazoline. The data are shown below.

| Example | Dye | Initial Voltage ($V_o$) (positive) | Time to Vo/2 (sec) |
|---|---|---|---|
| 50 | None | 585 | 6.0 |
| 51 | 2 | 400 | 1.2 |
| 52 | 4 | 445 | 1.3 |
| 53 | 5 | 475 | 1.2 |
| 54 | 7 | 465 | 1.4 |
| 55 | 8 | 415 | 1.0 |
| 56 | 17 | 440 | 1.2 |
| 57 | 18 | 420 | 1.5 |
| 58 | 21 | 450 | 1.2 |
| 59 | 23 | 445 | 1.1 |
| 60 | 25 | 505 | 1.8 |

We claim:

1. A sensitized photoconductive layer comprising a binder, at least 15% by weight of an electron donating compound and a sensitizing amount of a thiopyrylium compound of the general formula:

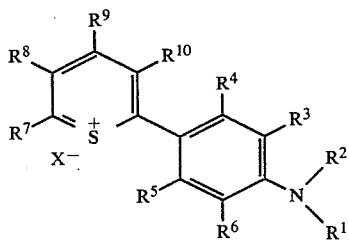

in which:
R$^1$ and R$^2$ are independently selected from the group consisting of a hydrogen atom, an alkyl or substituted alkyl group, an aryl or substituted aryl group, an aralkyl or substituted aralkyl group, a cycloaliphatic or substituted cycloaliphatic group, and a heterocyclic or substituted heterocyclic group of C, S, N and O atoms in 5, 6 or 7-membered rings providing R$^1$ and R$^2$ do not both represent cyclic groups of aromatic nature, and R$^1$ and R$^2$ together may represent the necessary atoms to complete a non-aromatic heterocyclic ring, R$^3$, R$^4$, R$^5$ and R$^6$ are independently selected from the group consisting of a hydrogen atom and any substituent providing the sum of their $\sigma_p$ constants has a value of less than +0.5, and R$^3$ and R$^4$ and/or R$^5$ and R$^6$ may represent the necessary atoms to complete an alicyclic or aromatic ring, and R$^3$ and R$^2$ and/or R$^1$ and R$^6$ represent the necessary atoms to complete a non-aromatic heterocyclic ring, R$^7$ and R$^9$ are independently selected from the group consisting of a hydrogen atom and any carbon linked substituent containing up to 16 carbon atoms, R$^8$ and R$^{10}$ are independently selected from the group consisting of a hydrogen atom, an alkyl group having 1 to 4 carbon atoms, and any two adjacent substituents R$^7$, R$^8$, R$^9$ and R$^{10}$ together may complete an alicyclic or aromatic ring, and X$^-$ represents an anion.

2. The element of claim 1 wherein said thiopyrylium compound is in the form of a particulate discontinuous phase present as at least 0.005 percent by weight of said layer.

3. The element claimed in claim 2 in which R, R$^4$, R$^5$ and R$^6$ independently are selected from the group consisting of a hydrogen atom and other substituent such that the sum of their $\sigma_p$ constants has a value less than +0.4.

4. The element claimed in claim 3 in which R$^3$, R$^4$, R$^5$ and R$^6$ are independently selected from the group consisting of H, alkyl, alkoxy, halogen and NH$_2$.

5. The element claimed in claim 1, 2, 3 or 4, in which R$^1$ and R$^2$ are independently selected from the group consisting of H, CH$_3$, C$_2$H$_5$, C$_6$H$_5$, C$_6$H$_5$CH$_2$, cyclo-C$_6$H$_{11}$ and CH$_2$CH$_2$OH.

6. The element claimed in claim 1, in which R$^8$=R$^{10}$=H and R$^7$=R$^9$=C$_6$H$_5$.

7. The element claimed in claim 4, in which R$^8$=R$^{10}$=H and R$^7$=R$^9$=C$_6$H$_5$.

8. The element of claim 1 wherein said thiopyrylium compound is in the form of a particulate discontinuous phase present as at least from 0.01 to 15 percent by weight of said layer.

* * * * *